United States Patent [19]

Takei et al.

[11] 4,287,085
[45] Sep. 1, 1981

[54] (2'-CYANO-4'-ALKYLPHENYL)-3-CYANO-4-ALKOXYBENZOATES AND LIQUID CRYSTAL COMPOSITION INCLUDING SAME

[75] Inventors: Katsumori Takei; Sadao Kanbe; Yoshio Shionozaki, all of Suwa, Japan

[73] Assignee: Kabushiki Kaisha Suwa Seikosha, Tokyo, Japan

[21] Appl. No.: 144,809

[22] Filed: Apr. 29, 1980

[30] Foreign Application Priority Data

May 1, 1979 [JP] Japan .................................. 54-53660
Jun. 11, 1979 [JP] Japan .................................. 54-73295
Oct. 17, 1979 [JP] Japan .................................. 54-133826

[51] Int. Cl.³ ........................ C07C 121/75; C09K 3/34
[52] U.S. Cl. ........................... 252/299.63; 260/465 D; 252/299.65; 252/299.64
[58] Field of Search .................... 260/465 D; 252/299

[56] References Cited
U.S. PATENT DOCUMENTS 3,953,491  4/1976  Steinstrasser et al. .......... 260/465 D
4,110,243  8/1978  Abert-Mellah et al. ............. 252/299

Primary Examiner—Dolph H. Torrence
Attorney, Agent, or Firm—Blum, Kaplan, Friedman, Silberman & Beran

[57] ABSTRACT

Ester compounds suitable for use in liquid crystal compositions are provided. The ester compounds are (2'-cyano-4'-alkylphenyl)-3-cyano-4-n-alkoxybenzoates represented by the general formula:

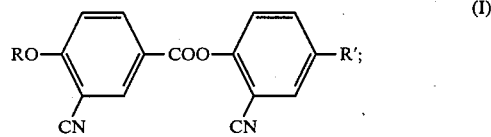

(I)

wherein R and R' each is a straight-chain alkyl group having one to eight carbon atoms. The ester compounds alone do not exhibit a liquid crystal phase, but have a relatively low melting point. Addition of at least one such ester compound to a liquid crystal composition lowers the value of the dielectric anisotropy of the composition at frequencies higher than the critical frequency, and lowers it at frequencies lower than the critical frequency. Such compositions are particularly well suited for the two-frequency matrix-addressing drive in a display of complex characters or graphic displays.

The ester compounds in accordance with the invention are prepared by condensing a 3-bromo-4-n-alkoxybenzoyl chloride having the general formula:

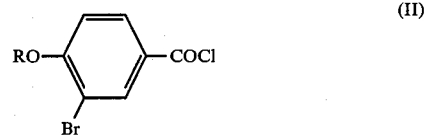

(II)

and a 2-cyano-4-n-alkylphenol having the general formula:

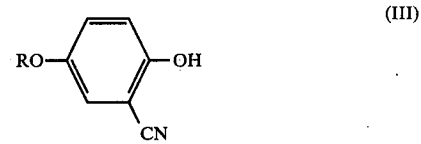

(III)

to prepare a (2'-cyano-4'-n-alkylphenol)-3-bromo-4-n-alkoxybenzoate having the general formula:

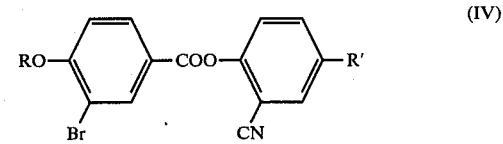

(IV)

wherein R and R' each is a straight-chain alkyl group having from one to eight carbon atoms, and reacting the benzoate (IV) with cuprous cyanide to yield the desired ester (I).

15 Claims, 8 Drawing Figures (2'-cyano-4'-n-butylpheyl)-3-cyano-4-n-heptyloxybenzoate (2'-cyano-4'-n-butylphenyl)-3-cyano-4-n-butyloxybenzoate

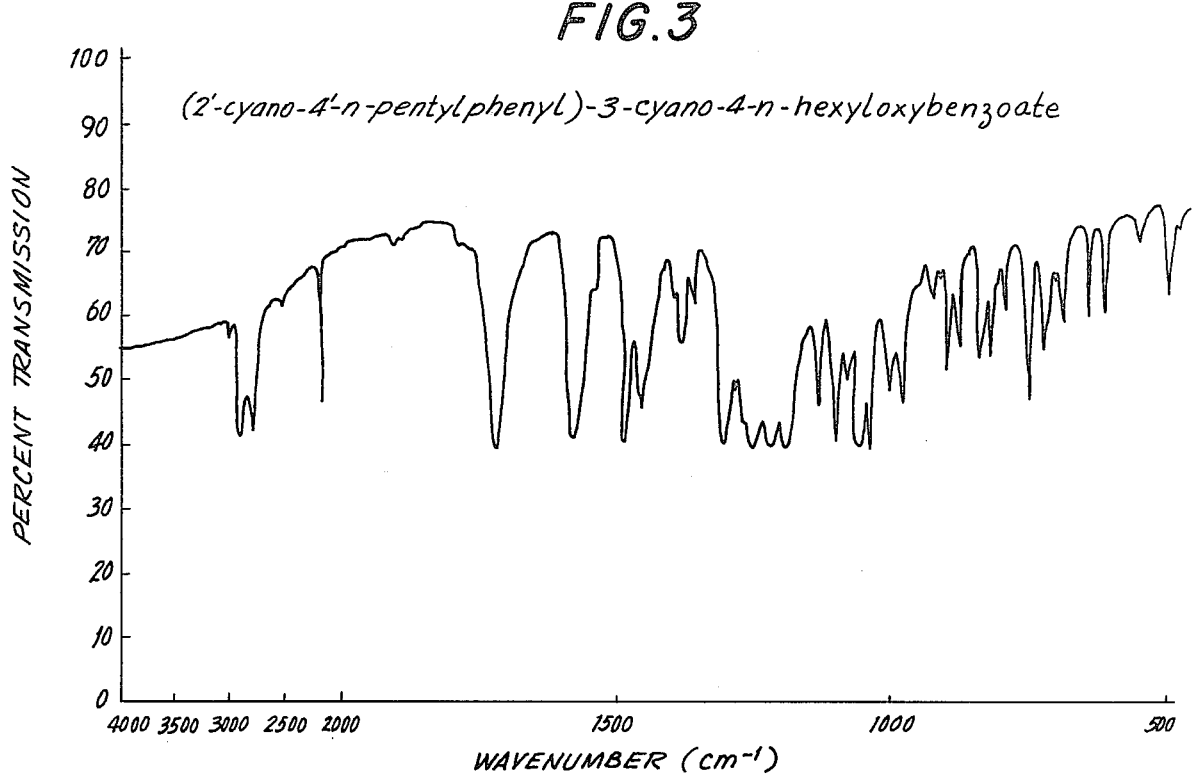
FIG.3 (2'-cyano-4'-n-pentylphenyl)-3-cyano-4-n-hexyloxybenzoate
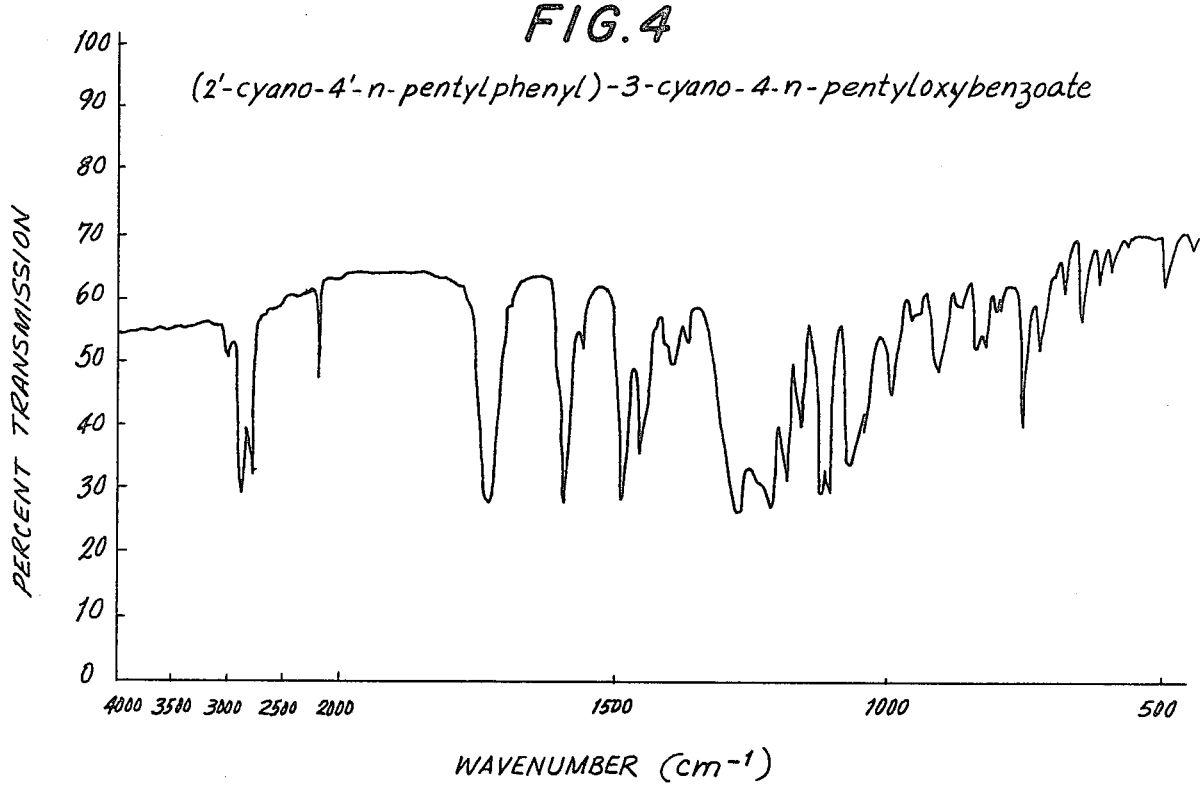
FIG.4 (2'-cyano-4'-n-pentylphenyl)-3-cyano-4-n-pentyloxybenzoate

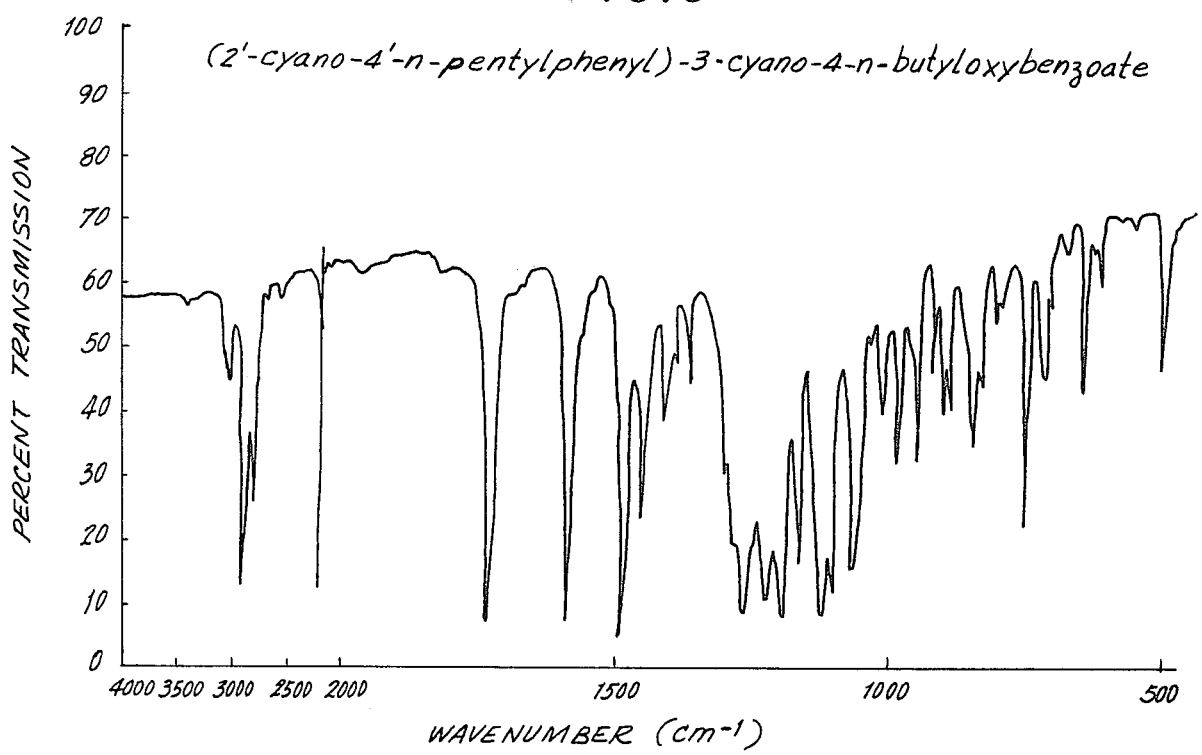
FIG.5
(2'-cyano-4'-n-pentylphenyl)-3-cyano-4-n-butyloxybenzoate
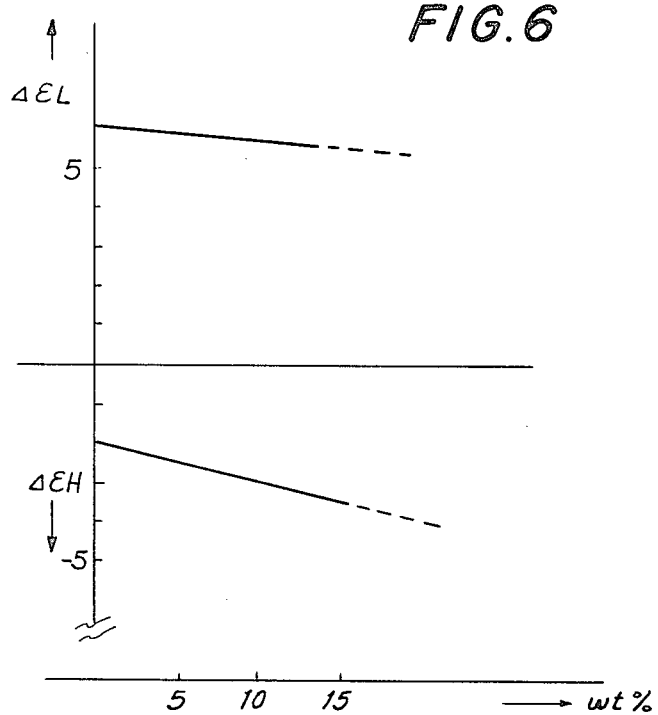
FIG.6
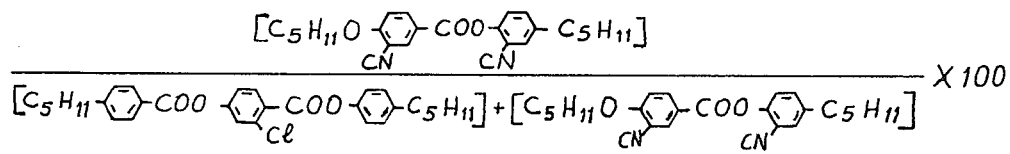

(2'-CYANO-4'-ALKYLPHENYL)-3-CYANO-4-ALKOXYBENZOATES AND LIQUID CRYSTAL COMPOSITION INCLUDING SAME

BACKGROUND OF THE INVENTION

This invention relates generally to new ester compounds, liquid crystal compositions containing the ester compound, methods of preparing the new ester compounds, and particularly to (2'-cyano-4'-n-alkylphenyl)-3-cyano-4-n-alkoxybenzoates.

Electro-optical display elements including liquid crystal compositions have been put into a variety of practical uses, in particular calculators, timepieces and the like. These liquid crystal display elements may be driven by various driving methods. A multiplexing drive is generally used to drive the liquid crystal displays, such as the generalized AC amplitudes selective mutliplexing method. However, such a method restricts the maximum number of rows which may be driven between eight and ten as a practical matter. Thus, there is difficulty in using the generalized AC amplitude selective multiplexing method to drive a television and a character display which are operated by addressing the multiplex matrix.

Recently, a method which takes advantage of the dielectric dispersion in the liquid crystal material has been found to be effective in elminating this disadvantage. However, when the multiplex matrix is addressed, by using the two-frequency matrix-addressing method, the energy consumption is high due to the fact that AC applied voltage is of high frequency and of high voltage. Thus, the two-frequency matrix-addressing method is less than completely satisfactory. It has been found that this energy consumption may be effectively reduced by making the driving voltage lower. It is known that the driving voltage V is dependent upon the dielectric anisotropy $\Delta\epsilon$ of the liquid crystal material used. This relationship has been defined as $$V \alpha \sqrt{\frac{1}{|\Delta E|}}$$

In other words, as the absolute value $|\Delta\epsilon|$ increases, the value of driving voltage V is reduced.

Accordingly, it is desirable to provide a liquid crystal composition having the desired characteristics. Such a liquid crystal composition would have an increased absolute value of the negative dielectric anisotropy at frequencies higher than the critical frequency of lower than the critical frequency.

SUMMARY OF THE INVENTION

Generally speaking, in accordance with the invention, an ester compound suitable for use in a liquid crystal composition, a liquid crystal composition including such an ester compound and a method of preparing the ester compound are provided. The new ester compound is a (2'-cyano-4'-n-alkylphenyl)-3-cyano-4-n-alkoxybenzoate which may be represented by the following general formula:

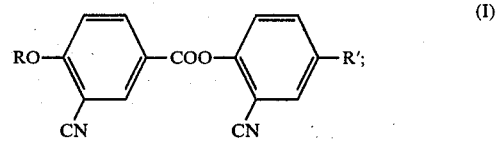

wherein R and R' each is a straight-chain alkyl group having from one to eight carbon atoms.

These ester compounds in accordance with the invention do not possess a liquid crystal phase. However, addition of a small amount of at least one of the ester compounds in accordance with the invention to a liquid crystal composition, yields a liquid crystal composition having an increased negative dielectric anisotropy in the frequency range higher than the critical frequency. Generally, between about at least an effective amount and 40 weight percent of at least one ester compound in accordance with the invention is added to the composition.

The ester compounds in accordance with the invention are prepared by condensing a 3-bromo-4-n-alkoxybenzoyl chloride having the general formula:

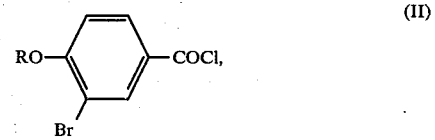

and a 2-cyano-4-n-alkylphenyl having the general formula:

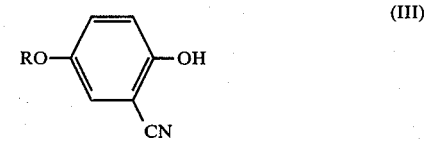

to yield a (2'-cyano-4'-n-butylphenyl)-3-bromo-4-n-heptyloxybenzoate having the general formula:

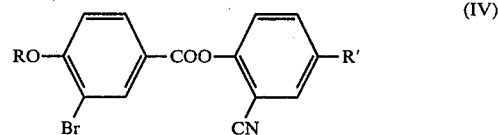

wherein R and R' each is a straight-chain alkyl group having from one to eight carbon atoms and reacting compound (IV) with cuprous cyanide to yield the ester (2'-cyano-4'-n-alkylphenyl)-3-cyano-4-n-alkoxybenzoate.

Accordingly, it is an object of the invention to provide (cyano-alkylphenyl)-cyano-alkoxybenzoate ester compounds.

Another object of the invention is to provide improved liquid crystal compositions including the esters.

A further object of the invention is to provide a method of preparing the new esters.

Still other objects and advantages of the invention will in part be obvious and will in part be apparent from the specification.

The invention accordingly comprises the several steps and the relation of one or more of such steps with respect to each of the others, and the composition possessing the features properties, and the relation of constituents, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a graphical representation of the infrared absorption spectrum of (2'-cyano-4'-n-pentylphenyl)-3-cyano-4-n-hexyloxybenzoate;

FIG. 4 is a graphical representation of the infrared absorption spectrum of (2'-cyano-4'-n-pentylphenyl)-3-cyano-4-n-pentyloxylbenzoate;

FIG. 5 is a graphical representation of the infrared absorption spectrum of (2'-cyano-4'-n-pentylphenyl)-3-cyano-4-n-butyloxybenzoate;

FIG. 6 is a graphical representation of the relationship between dielectric anisotropy at high frequencies above the critical frequency and low frequencies below the critical frequency when (2'-cyano-4'-n-pentylphenyl)-3-cyano-4-n-pentyloxybenzoate is added to p-n-pentylphenyl-2-chloro-4-(p-n-pentylbenzoyloxy)benzoate in varying weight percentages;

DESCRIPTION OF THE PREFERRED EMBODIMENTS

Figure 1:
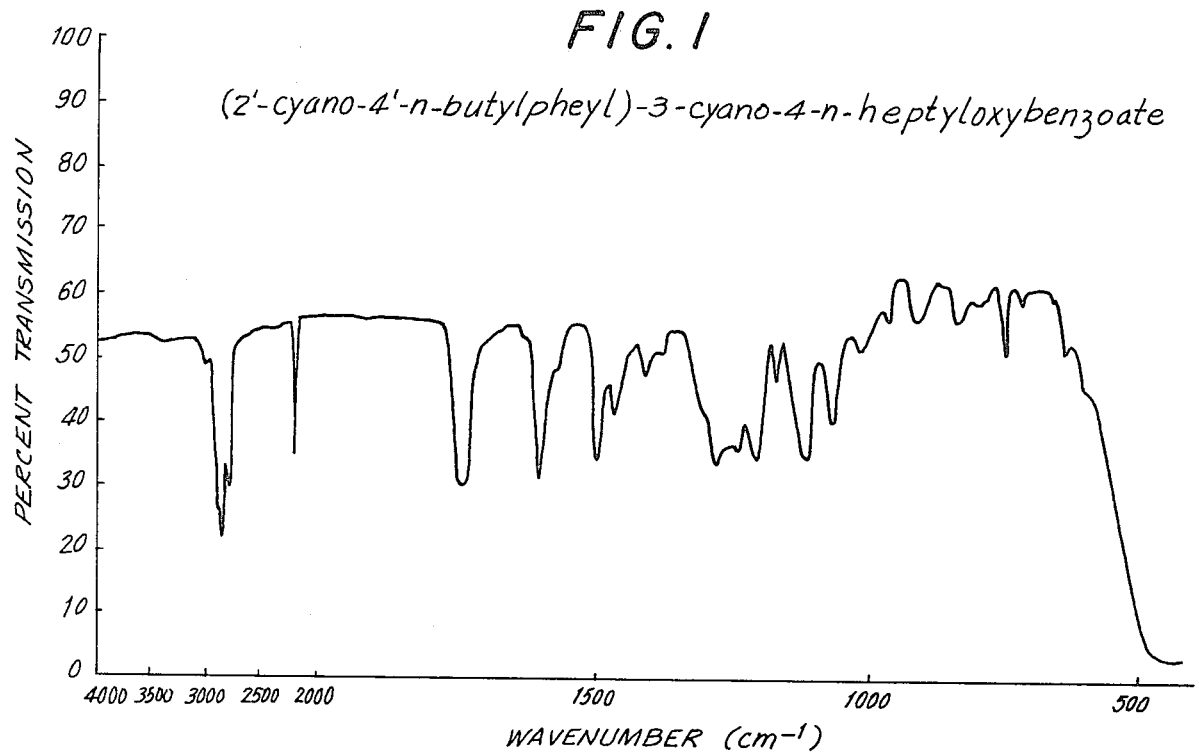
FIG. 1 is a graphical representation of the infrared absorption spectrum of (2'-cyano-4'-n-butylphenyl)-3-cyano-4-n-heptyloxybenzoate.
Figure 2:
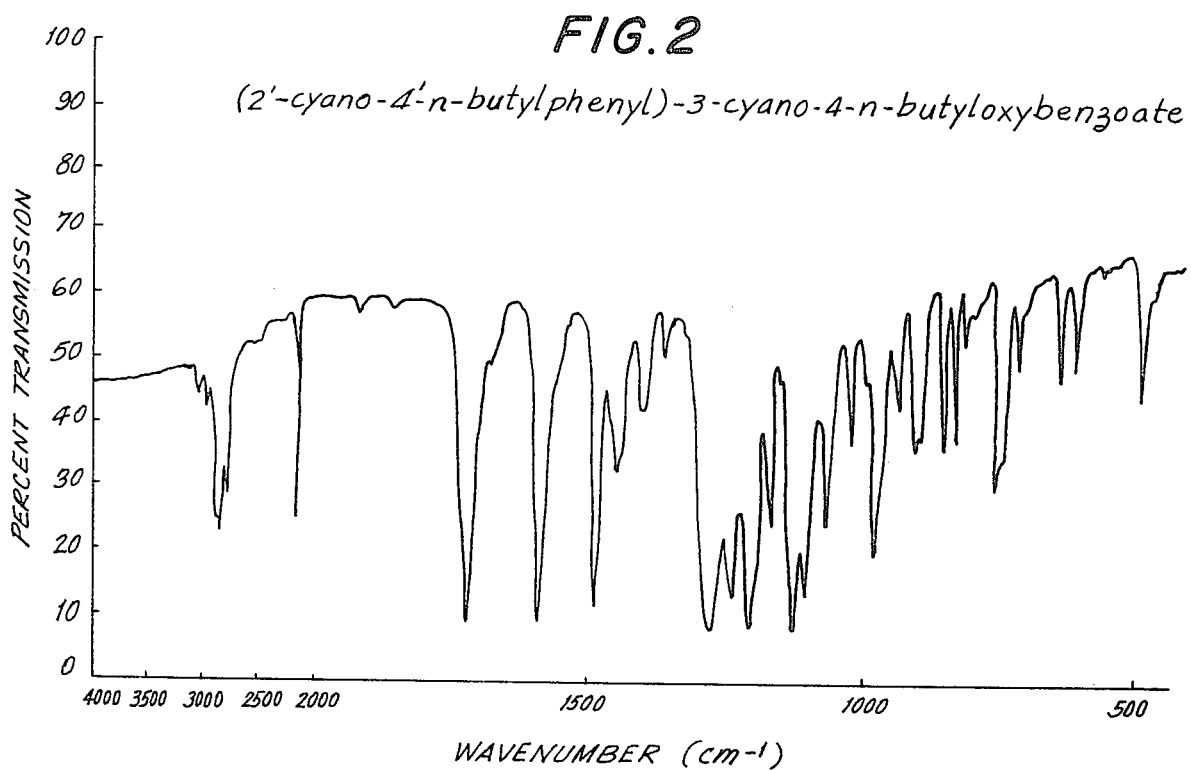
FIG. 2 is a graphical representation of the infrared absorption spectrum of (2'-cyano-4'-n-butylphenyl)-3-cyano-4-n-butyloxybenzoate.

The new ester compounds in accordance with the invention are (2'-cyano-4'-alkylphenyl)-3-cyano-4-n-alkylbenzoate represented by the general formula:

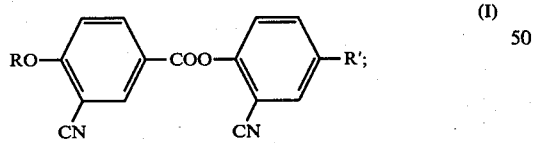

(I)

wherein R and R' each is a straight-chain alkyl group selected from the group consisting of straight-chain alkyl groups having between one and eight carbon atoms, inclusive.

These ester compounds (I) are prepared by using as starting materials p-hydroxybenzoic acid represented by the formula:

and a p-alkylphenyl represented by the formula:

wherein R' is a straight-chain alkyl group having from one to eight carbon atoms. The reaction steps are represented by the following reaction sequence:

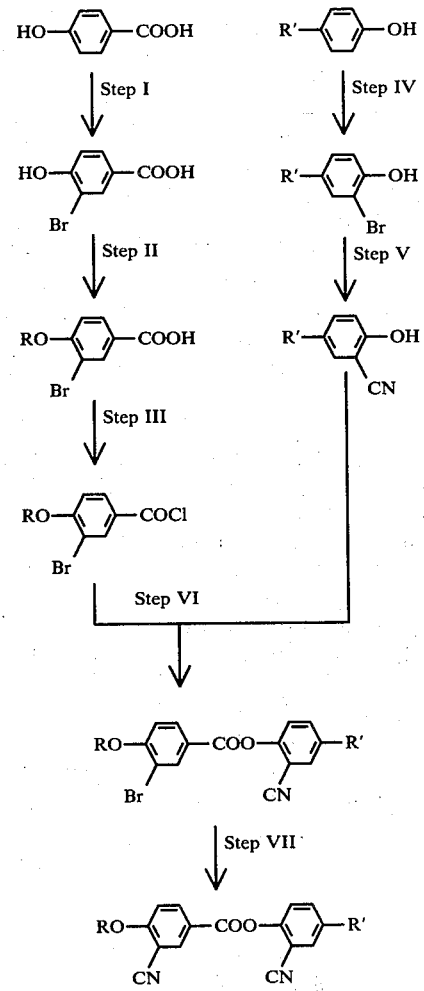

In each of the above formulas, R and R' each is a straight-chain alkyl group selected from the group consisting of straight-chain alkyl groups having from one to eight carbon atoms, inclusive. The steps in the reaction sequence are as follows:

Step I: 3-bromo-4-hydroxybenzoic acid is prepared by reacting p-hydroxybenzoic acid and bromine in glacial acetic acid.

Step II: 3-bromo-4-alkoxybenzoic acid is prepared by reacting the 3-bromo-4-hydroxybenzoic acid prepared in Step I and an alkyl bromide in ethanol with aqueous potassium hydroxide added as a catalyst.

Step III: 3-bromo-4-alkoxybenzoyl chloride is prepared by reacting the 3-bromo-4-alkoxybenzoic acid prepared in Step II and thionyl chloride.

Step IV: 2-bromo-4-alkylphenol is prepared by reacting a p-alkylphenol and bromine in glacial acetic acid.

Step V: 2-cyano-4-alkylphenol is prepared by reacting the 2-bromo-4-alkylphenol prepared in Step IV and cuprous cyanide in N-methyl-2-pyrrolidone.

Step VI: (2'-cyano-4'-alkylphenyl)-3-bromo-4-alkoxybenzoate is prepared by reacting the 3-bromo-4-alkoxybenzoyl chloride prepared in Step III and the 2-cyano-4-alkylphenol prepared in Step V in ether with pyridine added as a catalyst.

Step VII: (2'-cyano-4'-alkylphenyl)-3-cyano-4-alkoxybenzoate is prepared by reacting the (2'-cyano-4'-alkylphenyl)-3-bromo-4-alkoxybenzoate prepared in Step VI and cuprous cyanide in N,N-dimenthylformamide.

Preparation of the new ester compounds in accordance with the invention will be described in the following examples. In each case percentages set forth are by weight, based on the total weight of the mixture. The examples are set forth as illustrative, and not in a limiting sense. As noted above, R and R' each is an n-alkyl group of from one to eight carbon atoms. In the preferred species, the groups have from three to seven carbon atoms.

EXAMPLE 1

The ester (2'-cyano-4'-n-butylphenyl)-3-bromo-4-n-heptyloxybenzoate as represented by the general formula (I) wherein R is an n-heptyl group and R' is an n-butyl group was prepared as follows.

Step I 50 g (0.37 mol) of commercially available p-hydroxybenzoic acid was dissolved in 370 ml glacial acetic acid by heating with stirring. Heating was continued after the acid dissolved and 59 g (0.37 mol) bromine dissolved in 60 ml glacial acetic acid was rapidly added to the boiling solution to avoid bumping. The solution was refluxed for six hours with continuing stirring. Following reflux, the reaction solution was permitted to stand and cooled to room temperature. The cooled solution was poured into two liters of cold water. A white precipitate was formed. The white crystals were filtered by suction and were recrystalized with glacial acetic acid to yield 55.2 g of purified 3-bromo-4-hydroxybenzoic acid. The calculated yield was 70.3%.

Step II 25.8 g (0.119 mol) of the 3-bromo-4-hydroxybenzoic acid prepared in Step I was dissolved in 615 ml ethanol and 42.6 g (0.238 mol) of heptyl bromide was added to the solution. Aqueous potassium hydroxide (13.5 g of potassium hydroxide in 62 ml of water) was added with heating and the above solution was refluxed for ten hours. 125 ml of 10% aqueous potassium hydroxide was added and the solution was refluxed for two more hours. The reaction solution was allowed to stand to cool to room temperature, and excess 5 N hydrochloric acid solution was added commencing crystallization. The crystals were fractionated through filtration by suction, washed with water, dried and recrystallized with ethanol to yield 31.9 g of purified 3-bromo-4-n-heptyloxybenzoic acid. The yield was calculated to be 85.5%.

Step III 11 g of thionyl chloride was added to 14.5 g (0.046 mol) of the 3-bromo-4-n-heptyloxybenzoic acid prepared in Step II and was gently refluxed for two hours. Excess thionyl chloride was removed by distillation or vacuum distillation to yield 14.9 g of 3-bromo-4-n-heptyloxybenzoyl chloride. The yield was calculated to be 96.8%.

Step IV 22.5 g (0.15 mol) of commercially available p-n-butylphenol was dissolved in 100 ml glacial acetic acid and was slowly heated to 40° C. 24.5 g (0.153 mol) of bromine was added and the solution was stirred for four hours at 60° C. The glacial acetic acid in the reaction solution was removed by distillation and 31.7 g of 3-bromo-4-n-butylphenol was obtained from the residue by vacuum distillation (85° C./1 mmHg). The yield of 3-bromo-4-n-butylphenol was calculated to be 92.1%.

Step V 16.0 g (0.07 mol) of the 3-bromo-4-n-butylphenol prepared in Step IV was dissolved in 70 ml of N-methyl-2-pyrrolidone. 6.5 g (0.073 mol) cuprous cyanide was added to the suspension which was refluxed for four hours. The reaction mixture was cooled to room temperature and poured into a solution of 26 g ferric chloride hexahydrate dissolved in a mixed solution of 10 ml of concentrated hydrochloric acid and 47 ml of water. The resultant solution was stirred with heating for 30 minutes at 65° C. in order to decompose nitrile complexes with cuprous bromide. Next, the suspension was poured into 300 ml of cold water, and an organic layer which separated out was extracted with ether. After the organic layer was clearned with acid, alkali and water and was dehydrated with anhydrous sodium sulfate, ether in the organic layer was distilled off. The residue was distilled under vacuum (115° C./1 mmHg) to yield 8.4 g of purified 3-cyano-4-n-butylphenol. The yield was calculated to be 68.2%.

Step VI 4.2 g (0.024 mol) of the 3-cyano-4-n-butylphenol prepared in Step V was dissolved in 50 ml ether, and 6 ml pyridine was added as a catalyst. 9.7 g (0.029 mol) of the 3-bromo-4-n-heptyloxybenzoyl chloride solution prepared in Step III and 30 ml of ether was slowly added to the reaction solution with violently shaking in a water bath having floating ice cubes. After the addition, the reaction solution was allowed to stand at room temperature for a while and was refluxed for two hours. After completion of the reaction, the reaction mixture was filtered to remove inorganic salt. An organic layer was cleaned and dehydrated and the solvent was distilled off. The residue was recrystallized in hexane to yield 9.9 g of (2'-cyano-4'-n-butylphenyl)-3-bromo-4-n-heptyloxybenzoate. The calculated yield was 87.6%.

Step VII 9.9 g (0.021 mol) of the (2'-cyano-4'-n-butylphenyl)-3-bromo-4-n-heptyloxybenzoate prepared in Step VI and 4 g of cuprous cyanide were added to 80 ml of N,N-dimethylformamide. The suspension was gently refluxed for four hours. The reaction mixture was cooled to room temperature, poured into a solution of 14.5 g ferric chloride hexahydrate dissolved in a mixed solution of 3.6 ml of concentrated hydrochloric acid and 22 ml of water, and was stirred with heating at 65° C. for 30 minutes in order to decompose any complexes. An organic layer was extracted from the suspension with toluene, was cleaned and was dehydrated. The toluene was distilled off. The residue was recrystallized in ethanol to yield 3.4 g of purified (2'-cyano-4'-n-butylphenyl)-3-cyano-4-n-heptyloxybenzoate. The yield was calculated to be 39.1%.

EXAMPLE 2

The procedure followed in Example 1 was repeated to prepare (2'-cyano-4'-n-butylphenyl)-3-cyano-4-n-butyloxybenzoate. In this case in general formula (I) each R and R' is an n-butyl group. The yields of intermediary compounds were approximately the same as obtained in Example 1.

The following TABLE I sets forth the melting point of the intermediary compounds prepared in each step of the preparation in accordance with the invention as illustrated in Examples 1 and 2.

TABLE I

| compound | Example 1 | Example 2 |
|---|---|---|
| R | n-C$_7$H$_{15}$ | n-C$_4$H$_9$ |
| R' | n-C$_4$H$_9$ | n-C$_4$H$_9$ |
|  | 152° C. | |
|  | 129.5° C. | 154° C. |
|  | | 58° C. |
|  | 53° C. | 46° C. |

EXAMPLE 3

The ester (2'-cyano-4'-n-pentylphenyl)-3-cyano-4-n-pentyloxybenzoate was prepared in accordance with the procedures outlined in Example 1. The yields in each step were as follows.

Step I 50 g (0.37 mol) of commercially available p-hydroxybenzoic acid yielded 55.2 g purified 3-bromo-4-hydroxybenzoic acid, which was calculated to be a yield of 70.3%.

Step II 25.8 g (0.119 mol) of the 3-bromo-4-hydroxybenzoic acid was reacted with 36.0 g (0.238 mol) pentyl bromide to yield 29.8 g of purified 3-bromo-4-n-pentyloxybenzoic acid. The yield was calculated to be 87.2%.

Step III 20.1 g (0.070 mol) of the 3-bromo-4-n-pentyloxybenzoic acid prepared in Step II was reacted with 13 g thionyl chloride.

Step IV 24.6 g (0.15 mol) of p-n-pentylphenol was reacted with 24.5 g (0.153 mol) bromine in glacial acetic acid to yield 32.6 g of 2-bromo-4-n-pentylphenol by vacuum distillation or a yield of 89.5%.

Step V 17.0 g (0.07 mol) of the 2-bromo-4-n-pentylphenol prepared in Step IV was reacted with cuprous cyanide and N-methyl-2-pyrrolidine to yield 9.4 g of purified 3-cyano-4-n-pentylphenol. The yield was calculated to be 70.6%.

Step VI 4.5 g (0.024 mol) of the 2-cyano-4-n-pentylphenol prepared in Step V was reacted with 3-bromo-4-pentyloxybenzoyl chloride prepared in Step III in ether with pyridine as a catalyst to yield 84.6% or 9.3 g of (2'-cyano-4'-n-pentylphenyl)-3-bromo-4-n-pentyloxybenzoate.

Step VII 9.3 g (0.020 mol) of the (2'-cyano-4'-n-pentylphenyl)-3-bromo-4-n-pentyloxybenzoate prepared in Step VI was reacted with cuprous cyanide and N,N-dimethylformamide to yield 3.0 g of purified (2'-cyano-4'-n-pentylphenyl)-3-cyano-4-n-pentyloxybenzoate. The yield was calculated to be 36.7%.

EXAMPLE 4

The procedure followed in Example 1 was repeated to prepare (2'-cyano-4'-n-pentylphenyl)-3-cyano-4-n-hexyloxybenzoate. In this case, in general formula (I) R is n-hexyl and R' is n-pentyl.

EXAMPLE 5

The procedure followed in Example 1 was repeated to prepare (2'-cyano-4'-n-pentylphenyl)-3-cyano-4-n-butyloxybenzoate. In this case, in general formula (I) R is n-butyl and R' is n-pentyl.

The melting points of the ester compounds prepared in Examples 1-5, each represented by the general formula (I), are set forth in the following Table II.

TABLE II

| Example | Compound | Melting Point (°C.) | Infrared Absorption Spectrum - FIG. |
|---|---|---|---|
| 1 | 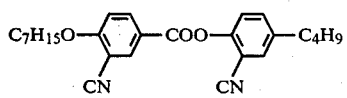 | 43 | 1 |
| 2 | 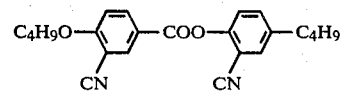 | 79 | 2 |

TABLE II-continued

| Example | Compound | Melting Point (°C.) | Infrared Absorption Spectrum - FIG. |
|---|---|---|---|
| 3 | $C_5H_{11}O$—⟨Ph(CN)⟩—COO—⟨Ph(CN)⟩—$C_5H_{11}$ | 66.5 | 4 |
| 4 | $C_6H_{13}O$—⟨Ph(CN)⟩—COO—⟨Ph(CN)⟩—$C_5H_{11}$ | 52.5 | 3 |
| 5 | $C_4H_9O$—⟨Ph(CN)⟩—COO—⟨Ph(CN)⟩—$C_5H_{11}$ | 78 | 5 |

As noted in Table II, graphical representations of the infrared absorption spectrums of each of the ester compounds are shown in FIGS. 1–5, respectively.

As shown in Table II, the ester compounds themselves do not exhibit a liquid crystal phase. However, as the molecules are stick-shaped, they may be mixed with liquid crystal materials, as they have an orientation and anisotropy similar to the liquid crystal materials. Each of the ester compounds has a relatively low melting point, so that a substantial amount of ester can be added to the liquid crystal composition, which will retain the characteristics of the liquid crystal material in a more-stable condition. As the ester compounds prepared in accordance with the invention have two cyano bases at an angle of about 60° to the main axis of the molecule, when added to a liquid crystal material even in a minor amount, the ester compound can import negative dielectric anisotropy to the liquid crystal composition.

In other words, addition of a small amount of an ester compound prepared in accordance with the invention to a liquid crystal composition increases the absolute value of the negative dielectric anisotropy of the liquid crystal composition in the high-frequency range at frequencies above the critical frequency. Additionally, this addition decreases the value of the dielectric anisotropy in the low-frequency range at frequencies less than the critical frequency. Thus, using a liquid crystal composition including an ester compound in accordance with the invention in an electro-optical display element driven by the two-frequency matrix-addressing method reduces the driving voltage, thereby decreasing the energy consumption. Utilization of such liquid crystal compositions in positive-type guest-host display elements also exhibits the same beneficial effect.

Examples of the liquid crystal materials that can be mixed with the ester compounds prepared in accordance with the invention are set forth in the following Table III.

TABLE III

| Liquid Crystal Compound | Melting Clear Pt. (°C.) to Pt. (°C.) |
|---|---|
| $n\text{-}C_5H_{11}$—⟨Ph⟩—COO—⟨Ph(Cl)⟩—COO—⟨Ph⟩—$C_5H_{11}\text{-}n$ | 39.6 to 123 |
| $n\text{-}C_7H_{15}$—⟨Ph⟩—COO—⟨Ph(Cl)⟩—COO—⟨Ph⟩—$C_5H_{11}\text{-}n$ | 39.5 to 101 |
| $n\text{-}C_8H_{17}$—⟨Ph⟩—COO—⟨Ph(Cl)⟩—COO—⟨Ph⟩—$C_5H_{11}\text{-}n$ | 35.5 to 103.5 |
| $n\text{-}C_7H_{15}$—⟨Ph⟩—COO—⟨Ph⟩—COO—⟨Ph(Cl)⟩—CN | 85 to 196 |
| $n\text{-}C_6H_{13}O$—⟨Ph⟩—COO—⟨Ph⟩—COO—⟨Ph(Cl)⟩—CN | 96 to 214 |
| $C_2H_5$—⟨H⟩—COO—⟨Ph(Cl)⟩—COO—⟨Ph⟩—$C_5H_{11}\text{-}n$ | 50.3 to 116.6 |
| $n\text{-}C_8H_{17}$—⟨Ph⟩—COO—⟨Ph(Cl)⟩—⟨Ph⟩—$C_8H_{17}\text{-}n$ | 36 to 86 |

TABLE III-continued

| Liquid Crystal Compound | Melting Pt. (°C.) to | Clear Pt. (°C.) |
|---|---|---|
| 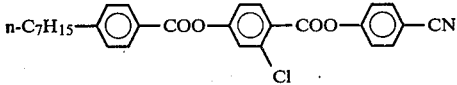 | 69 to 160 | |
| 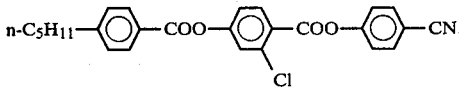 | 78 to 180 | |
| 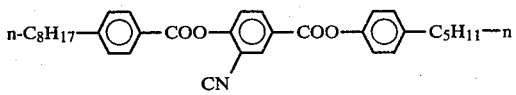 | 97 to 113 | |
| 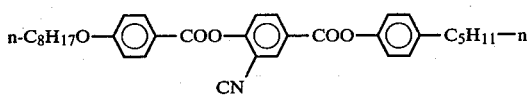 | 99 to 136 | |
| 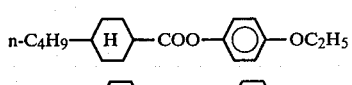 | 35.5 to 74 | |
| 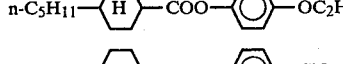 | 34 to 72 | |
| 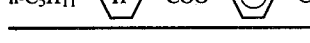 | 46.5 to 77.5 | |

The liquid crystal compounds set forth in Table III are only set forth for purposes of illustration. In addition to those shown, the conventionally well-known liquid crystal compounds, such as biphenyl, azoxy and Schiff bases and the like, can be utilized in combination with the ester compounds prepared in accordance with the invention.

When a minor amount of the ester compound (2'-cyano-4'-n-pentylphenyl)-3-cyano-4-n-pentyloxybenzoate in accordance with the invention is added to the liquid crystal material, p-n-pentylphenyl-2-chloro-4-(p-n-pentylbenzoyloxy) benzoate [EASTMAN KODAK 11650], the dielectric anisotropy measured in the low-frequency range or in the high-frequency range is as shown in FIG. 6. As shown in FIG. 6, the absolute value of the dielectric anisotropy in the high-frequency range above the critical frequency is increased. Additionally, the dielectric anisotropy in the low-frequency range below the critical frequency is also reduced.

When an ester compound prepared in accordance with the invention is added to a liquid crystal composition, generally between about a minor effective amount to about 40 weight percent of the ester compound is added. Preferably, between up to about 20 weight percent of at least one of the ester compounds is added.

EXAMPLE 6

A liquid crystal composition including the following materials was prepared in order to examine the difference in dielectric anisotropy at high and low frequencies. The liquid crystal composition included the following materials in the following weight percentages as set forth in Table IV.

TABLE IV

| Compounds | Weight % |
|---|---|
| 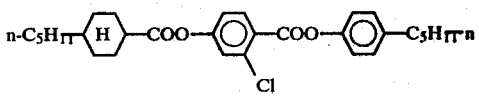 | 7.9 |
| 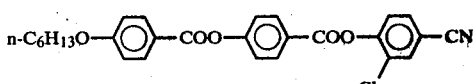 | 5.5 |
| 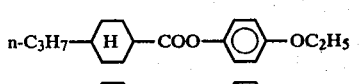 | 15.7 |
| 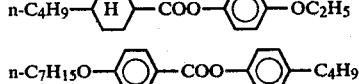 | 15.8 |
| 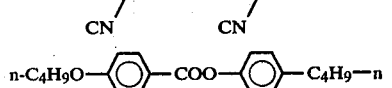 | 7.8 |
| 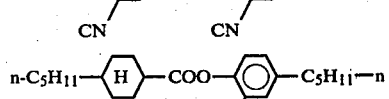 | 7.9 |
| 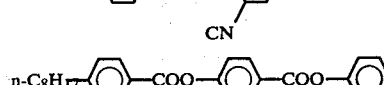 | 7.9 |
| 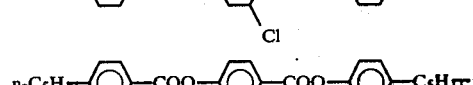 | 11.8 |
| 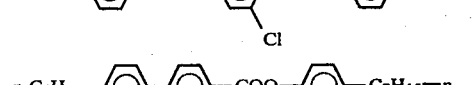 | 11.8 |
| 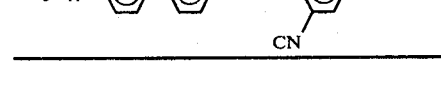 | 7.9 |

Figure 7:
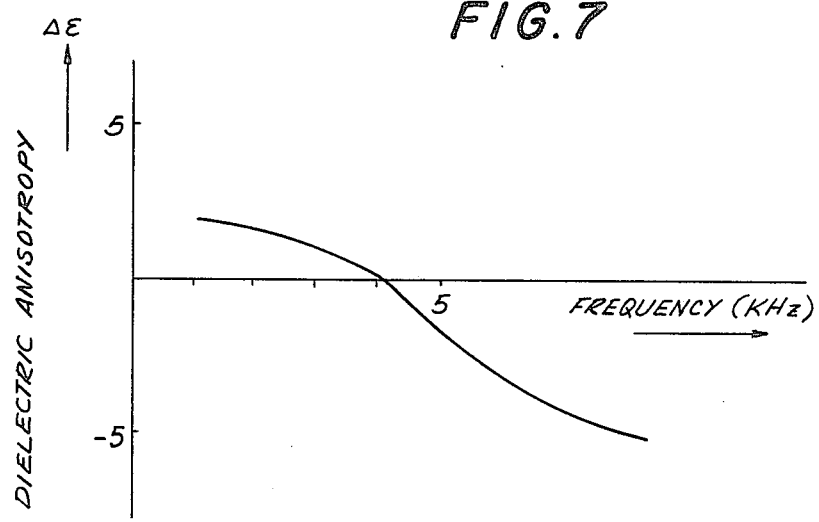
FIG. 7 is a graphical illustration of the relationship between dielectric anisotropy and frequency for the liquid crystal composition of Example 1.

The graphical representation of the dielectric anisotropy versus frequency characteristics is set forth in FIG. 7. In FIG. 7, the ordinate sets forth the dielectric anisotropy and the abscissa shows the frequency. Based on these experimental results, it can be seen that the dielectric anisotropy in the overtone region is about −5. This value is much lower than that of a conventional liquid crystal material and indeed much better.

EXAMPLE 7

A liquid crystal composition including the material set forth in Table V was prepared.

TABLE V

| Compounds | Weight % |
|---|---|
| n-C₇H₁₅—⌬—⌬—COO—⌬(Cl)—⌬ | 6.2 |
| n-C₆H₁₃O—⌬—COO—⌬(Cl)—COO—⌬—CN | 5.5 |
| n-C₃H₇—⟨H⟩—COO—⌬—OC₂H₅ | 16.0 |
| n-C₄H₉—⟨H⟩—COO—⌬—OC₂H₅ | 16.0 |
| n-C₇H₁₅O—⌬(CN)—COO—⌬(CN)—C₄H₉—n | 8.4 |
| n-C₄H₉O—⌬(CN)—COO—⌬(CN)—C₄H₉—n | 8.4 |
| n-C₅H₁₁—⌬—COO—⌬(CN)—C₅H₁₁—n | 7.0 |
| n-C₈H₁₇—⌬—COO—⌬(Cl)—COO—⌬—C₅H₁₁—n | 12.0 |
| n-C₅H₁₁—⌬—COO—⌬(Cl)—COO—⌬—C₅H₁₁—n | 12.0 |
| n-C₅H₁₁—⌬—⌬—COO—⌬(CN)—C₇H₁₅—n | 8.5 |

Figure 8:
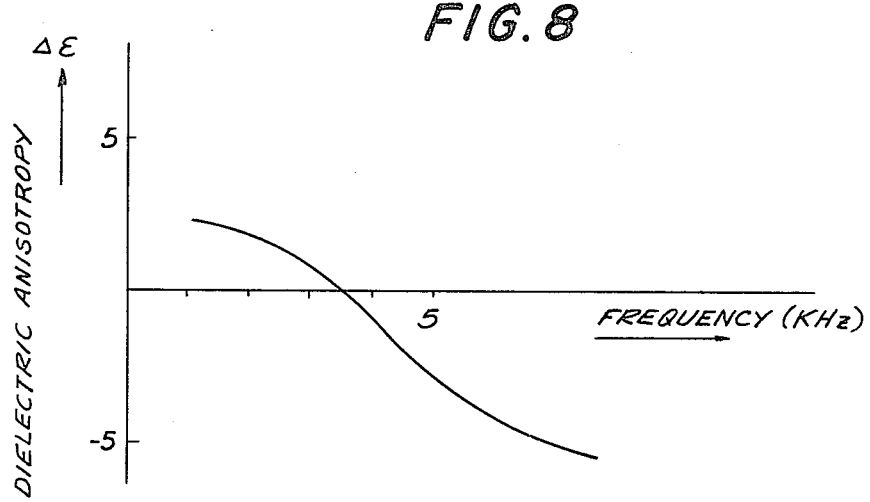
FIG. 8 is a graphical illustration of the relationship between the dielectric anisotropy and frequency for the liquid crystal composition of Example 2.

The dielectric anisotropy for this liquid crystal composition is shown in FIG. 8. When the liquid crystal compositions of Examples 7 and 8 are placed in a liquid crystal display cell driven by a two-frequency matrix-addressing method to drive the matrix, 32 rows can be driven. In addition, if the visual angle is reduced, it is possible to drive as many as 64 rows. Thus, a liquid crystal display device including a liquid crystal composition including an ester compound in accordance with the invention can be used to display complex characters of portions of display of televisions and electronic equipment when the multiplex matrix is addressed.

Accordingly, new ester compounds, namely, (2′-cyano-4′-alkylphenyl)-3-cyano-4-n-alkoxybenzoates represented by the general formula:

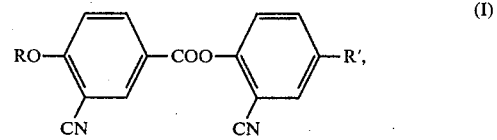

are provided in accordance with the invention. In the general formula, R and R′ is an alkyl group selected from the group consisting of straight-chain alkyl groups having from 1 to 8 carbon atoms. In the preferred species, R and R′ each is an alkyl group having from 3 to 7 carbon atoms. As noted above, the ester compounds themselves do not exhibit a liquid crystal phase, but have a beneficial effect on dielectric anisotropy when admixed with other liquid crystal material to form a liquid crystal composition in accordance with the invention.

When preparing such a liquid crystal composition, between at least an effective amount and up to about 40 weight percent of the ester compounds are included in the liquid crystal compositions. Preferably, from between up to about 20 weight percent is included. The ester compounds may be added to conventional liquid crystal materials, such as biphenyl, azoxy and Schiff bases. Preferably, the ester compounds are admixed with liquid crystal materials exhibiting an inversion of dielectric anisotropy about a critical frequency in order to lower the value of the negative dielectric anisotropy of the liquid crystal composition in the high-frequency range. These liquid crystal compositions are particularly well suited for use in the two-frequency matrix-addressing drive method.

It will thus be seen that the objects set forth above, among those made apparent from the preceding description, are efficiently attained, and since certain changes may be made in the products, in carrying out the above method and in the compositions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. An ester compound represented by the general formula

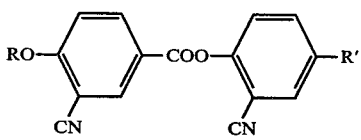

wherein each R and R' is selected from the group consisting of straight-chain alkyl groups having from one to eight carbon atoms for defining a (2'-cyano-4'-n-alkylphenyl)-3-cyano-4-n-alkoxybenzoate.

2. The ester compound of claim 1, wherein each R and R' is selected from the group consisting of straight-chain alkyl groups having from four to seven carbon atoms.

3. The ester compound of claim 1, wherein R is a straight-chain alkyl group having seven carbon atoms and R' is a straight-chain alkyl group having four carbon atoms for defining (2'-cyano-4'-n'butylphenyl)-3-cyano-4-n-heptyloxybenzoate.

4. The ester compound of claim 1, wherein each R and R' is a straight-chain alkyl group having four carbon atoms defining (2'-cyano-4'-n-butylphenyl)-3-cyano-4-n-butyloxybenzoate.

5. The ester compound of claim 1 wherein each R and R' is a straight-chain alkyl group having five carbon atoms for defining (2'-cyano-4'-n-pentylphenyl)-3-cyano-4-n-pentyloxybenzoate.

6. The ester compound of claim 1, wherein R is a straight-chain alkyl group having seven carbon atoms and R' is a straight-chain alkyl group having five carbon atoms for defining (2'-cyano-4'-n-pentylphenol-3-cyano-4-n-hexyloxybenzoate.

7. The ester compound of claim 1, wherein R is a straight-chain alkyl group having four carbon atoms and R' is a straight-chain alkyl group having five carbon atoms for defining (2'-cyano-4'-n-pentylphenyl)-3-cyano-4-n-butyloxybenzoate.

8. A liquid crystal composition comprising liquid crystal material including at least one frequency-dependent liquid crystal compound inducing a dielectric dispersion at lower frequency, admixed with at least one (2'-cyano-4'-alkylphenyl)-3-cyano-4-alkyloxbenzoate represented by the general formula:

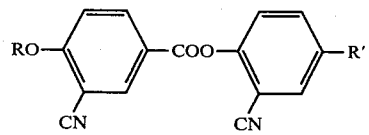

wherein each R and R' is selected from the group consisting of straight-chain alkyl groups having from one to eight carbon atoms for increasing the absolute value of the negative dielectric anisotropy of the liquid crystal compound in the high frequency range.

9. The liquid crystal composition of claim 8, wherein said liquid crystal material has a positive dielectric anisotropy in the low frequency range lower than the critical frequency and a negative dielectric anisotropy in the high frequency range above the critical frequency.

10. The liquid crystal composition of claim 9, wherein said at least one benzoate is present between the effective amount to about 40 weight percent, based on the total weight of the composition.

11. The liquid crystal composition of claim 9, wherein said at least one benzoate is present in from an effective amount to about 20 weight percent, based on the total weight of the composition.

12. A liquid crystal composition including at least one liquid crystal compound selected from the group consisting of:

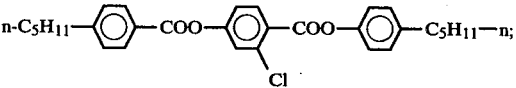

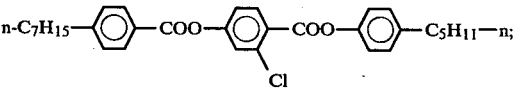

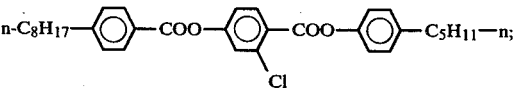

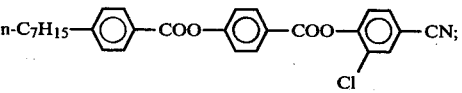

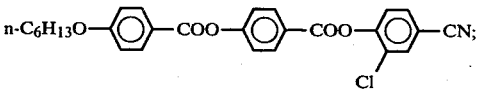

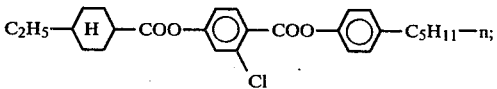

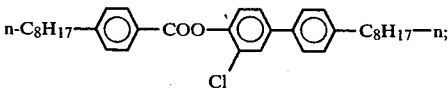

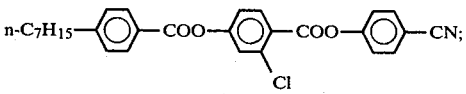

-continued

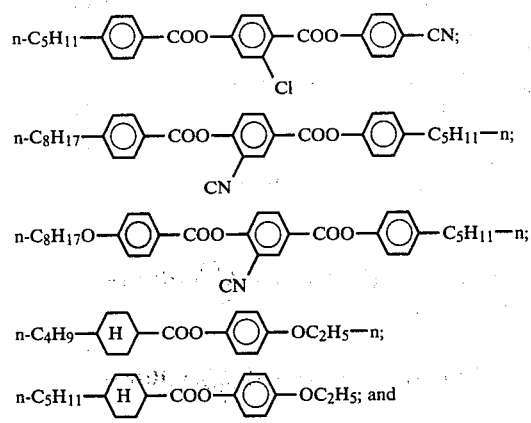

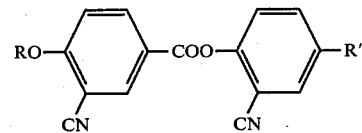

wherein each R and R' is selected from the group consisting of straight-chain alkyl groups having from one to eight carbon atoms for increasing the absolute value of the negative dielectric anisotropy of the liquid crystal compound in the high frequency range.

13. The liquid crystal composition of claim 8, wherein said liquid crystal material includes at least one liquid crystal compound selected from the group consisting of biphenyl, azoxy compounds and Schiff bases.

14. A liquid crystal composition comprising:

| Compound | Weight % |
|---|---|
| n-C$_5$H$_{11}$—⟨H⟩—COO—⌬—COO—⌬—C$_5$H$_{11}$-n (Cl) | 7.9 |
| n-C$_5$H$_{13}$O—⌬—COO—⌬—COO—⌬—CN (Cl) | 5.5 |
| n-C$_3$H$_7$—⟨H⟩—COO—⌬—OC$_2$H$_5$ | 15.7 |
| n-C$_4$H$_9$—⟨H⟩—COO—⌬—OC$_2$H$_5$ | 15.8 |
| n-C$_7$H$_{15}$O—⌬—COO—⌬—C$_4$H$_9$-n (CN, CN) | 7.8 |
| n-C$_4$H$_9$O—⌬—COO—⌬—C$_4$H$_9$-n (CN, CN) | 7.9 |
| n-C$_5$H$_{11}$—⟨H⟩—COO—⌬—C$_5$H$_{11}$-n (CN) | 7.9 |
| n-C$_8$H$_{17}$—⌬—COO—⌬—COO—⌬—C$_5$H$_{11}$-n (Cl) | 11.8 |
| n-C$_5$H$_{11}$—⌬—COO—⌬—COO—⌬—C$_5$H$_{11}$-n (Cl) | 11.8 |
| n-C$_5$H$_{11}$—⌬—⌬—COO—⌬—C$_7$H$_{15}$-n (CN) | 7.9 |

15. A liquid crystal composition comprising:

| Compound | Weight % |
|---|---|
| n-C$_7$H$_{15}$—⌬—⌬—COO—⌬—⌬ (Cl) | 6.2 | and admixed with at least one (2'-cyano-4'-alkylphenyl)-3-cyano-4-alkyloxybenzoate represented by the general formula:

-continued

| Compound | Weight % |
|---|---|
| n-C_6H_13O–⌬–COO–⌬–COO–⌬(Cl)–CN | 5.5 |
| n-C_3H_7–[H]–COO–⌬–OC_2H_5 | 16.0 |
| n-C_4H_9–[H]–COO–⌬–OC_2H_5 | 16.0 |
| n-C_7H_15O–⌬(CN)–COO–⌬(CN)–C_4H_9-n | 8.4 |
| n-C_4H_9O–⌬(CN)–COO–⌬(CN)–C_4H_9-n | 8.4 |
| n-C_5H_11–⌬–COO–⌬(CN)–C_5H_11-n | 7.0 |
| n-C_8H_17–⌬–COO–⌬(Cl)–COO–⌬–C_5H_11-n | 12.0 |
| n-C_5H_11–⌬–COO–⌬(Cl)–COO–⌬–C_5H_11-n | 12.0 |
| n-C_5H_11–⌬–⌬–COO–⌬(CN)–C_7H_15-n | 8.5 |

* * * * *